United States Patent [19]
Davison et al.

[11] Patent Number: 5,279,582
[45] Date of Patent: Jan. 18, 1994

[54] RETRACTABLE SYRINGE SHEATH WITH BOTTLE ENGAGEMENT

[76] Inventors: Thomas R Davison, 7658 Doubloon, SE., Grand Rapids, Mich. 49546; Alan R. Leist, deceased, late of Grand Rapids, Mich.; by Judith L. Leist, executrix, 11584 Woodgate NW., Grand Rapids, Mich. 49504

[21] Appl. No.: 861,552

[22] Filed: Apr. 1, 1992

[51] Int. Cl.⁵ .............................................. A64M 5/32
[52] U.S. Cl. ................................... 604/198; 604/263; 604/411
[58] Field of Search .............. 604/187, 192, 197, 198, 604/208, 263, 411, 414; 206/364, 365, 571

[56] References Cited

U.S. PATENT DOCUMENTS

| | | |
|---|---|---|
| D. 321,053 | 10/1991 | Baum . |
| 2,474,496 | 6/1949 | Rayman . |
| 2,695,023 | 11/1954 | Brown . |
| 2,869,540 | 1/1956 | Helmer et al. . |
| 2,943,624 | 7/1960 | Alquist . |
| 3,844,318 | 10/1974 | Raia et al. . |
| 3,853,158 | 12/1974 | Whitty . |
| 3,875,979 | 4/1975 | Hults . |
| 3,965,945 | 6/1976 | Ross . |
| 4,219,055 | 8/1980 | Wright . |
| 4,252,159 | 2/1981 | Maki . |
| 4,357,971 | 11/1982 | Friedman . |
| 4,466,426 | 8/1984 | Blackman . |
| 4,564,054 | 1/1986 | Gustavson ..................... 604/198 |
| 4,623,344 | 11/1986 | Eriksson . |
| 4,660,570 | 4/1987 | Dombrowski ................ 604/198 |
| 4,702,738 | 10/1987 | Spencer ........................ 604/263 |
| 4,778,454 | 10/1988 | LaDow . |
| 4,810,248 | 3/1989 | Masters et al. ............... 604/263 |
| 4,872,494 | 10/1989 | Coccia ........................... 604/411 |
| 4,883,101 | 11/1989 | Strong . |
| 4,932,940 | 6/1990 | Walker et al. ................ 604/198 |
| 4,969,876 | 11/1990 | Patterson ...................... 604/198 |
| 4,985,021 | 1/1991 | Straw et al. ................... 604/198 |
| 4,998,570 | 3/1991 | Strong . |
| 5,057,086 | 10/1991 | Dillard et al. ................ 604/198 |
| 5,061,251 | 10/1991 | Juhasz ........................... 604/198 |
| 5,147,303 | 9/1992 | Martin .......................... 604/198 |

*Primary Examiner*—John D. Yasko
*Assistant Examiner*—Anthony Gutowski
*Attorney, Agent, or Firm*—Warner, Norcross & Judd

[57] ABSTRACT

A safety hypodermic device includes a protective sleeve carried on the barrel of a syringe or the needle holder of an intravenous line. The sleeve has an extended position which envelops and protects the needle and a retracted position which exposes the needle for injection purposes. A coil spring carried on the barrel urges the sleeve toward the extended position. The open end of the sleeve may be provided with internal resilient tabs and a flange for receiving and grasping the head of a medicine bottle and for allowing the needle to penetrate the medicine bottle to the proper depth for filling. The spring may extend into the interior of the sleeve and abut against an internal rim of the sleeve. The plunger and barrel may be provided with tactile feedback to enable a visually impaired person to determine the amount of medicine being filled or dispensed.

8 Claims, 3 Drawing Sheets

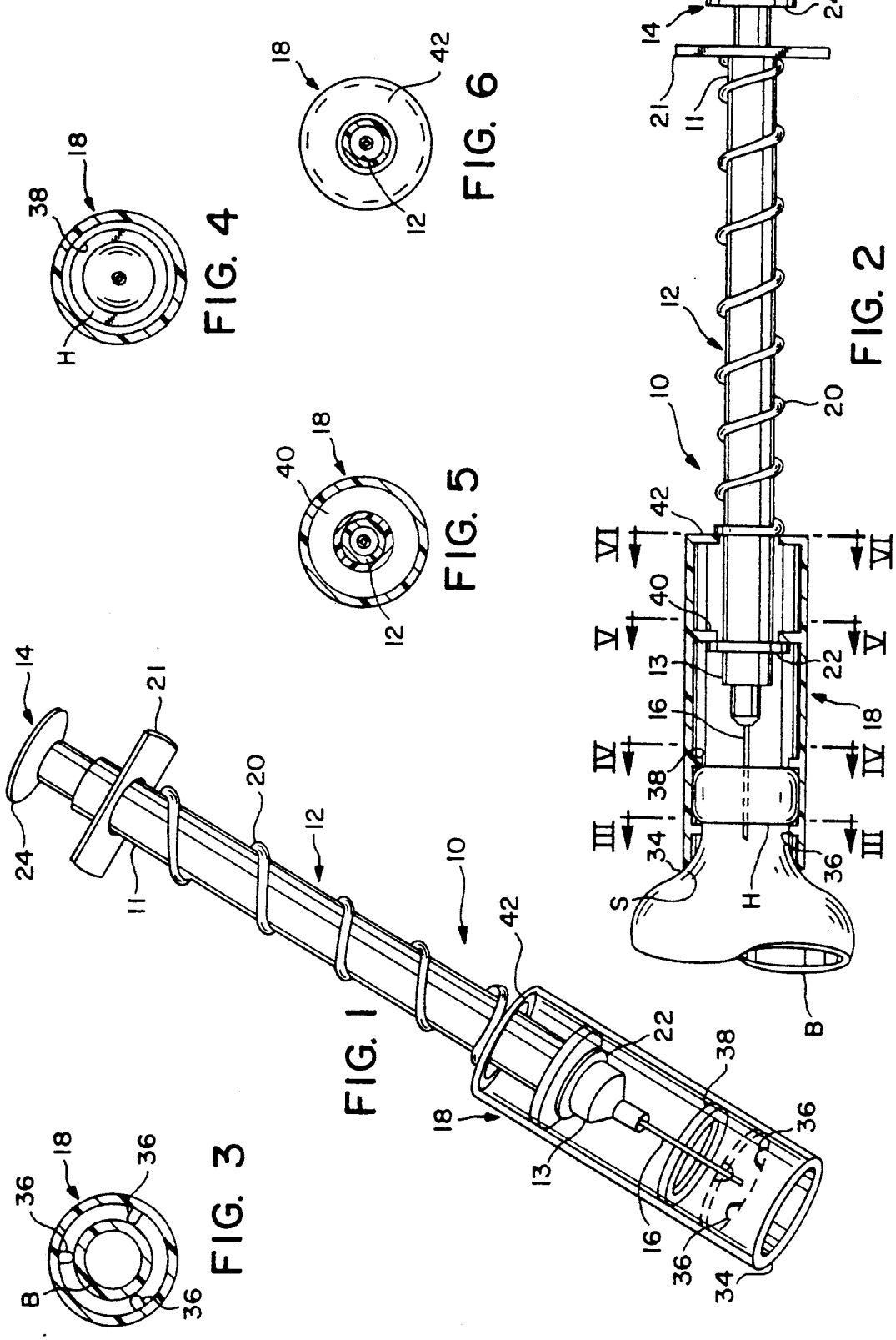

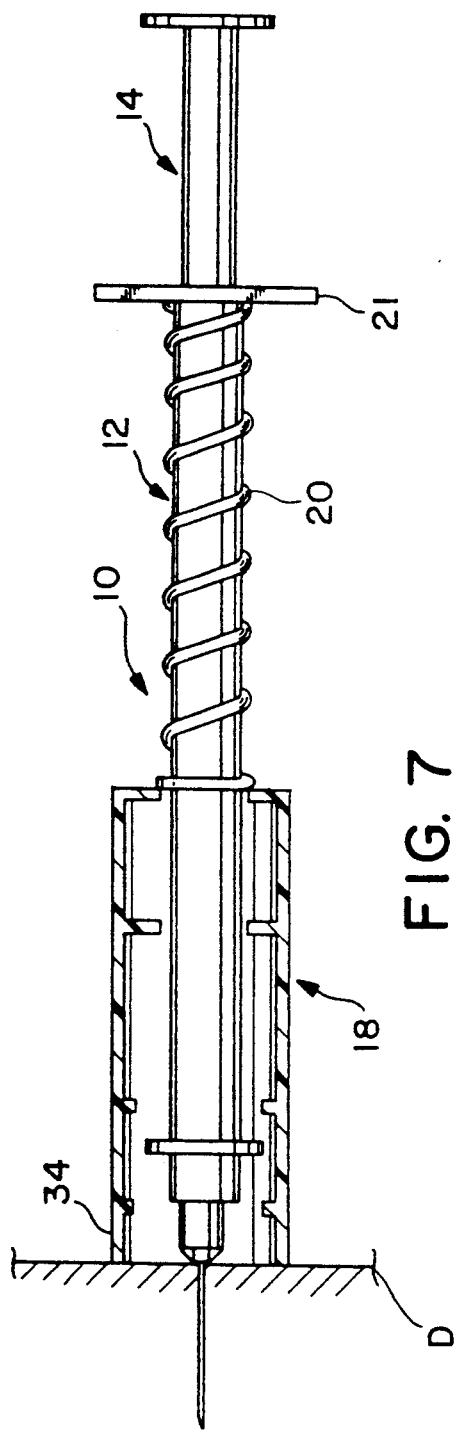
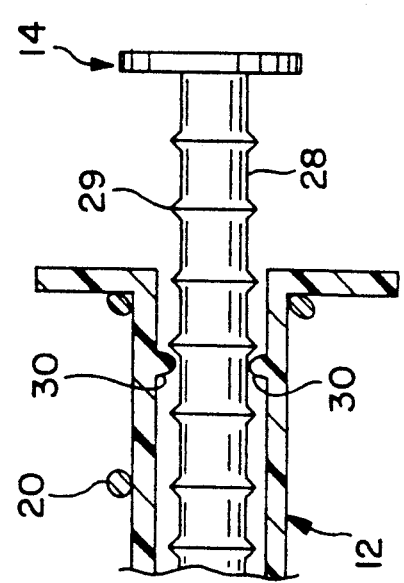
FIG. 7
FIG. 8

RETRACTABLE SYRINGE SHEATH WITH BOTTLE ENGAGEMENT

BACKGROUND OF THE INVENTION

1. Field of the Invention

The present invention relates to hypodermic syringes, and more particularly, to a hypodermic syringe having a protective sleeve.

2. Description of the Related Art

Hypodermic devices have become a major factor in health care not only for injectable drugs but also in drawing blood, other bodily fluids and tissue samples, as well as in the introduction of intravenous tubes, catheters, et al. into patients requiring health care or investigation of health problems.

Hypodermic syringes have become a way of life for many diabetics, who often must give themselves insulin injections one or more times each day. Most diabetic persons prefer to give these injections to themselves to avoid reliance on a caregiver and to prevent drawing attention to their diabetic condition. Unfortunately, a frequent consequence of diabetes is visual impairment. Giving oneself an insulin injection can be difficult to impossible, depending on the extent of the visual impairment, because visual impairment reduces or eliminates the diabetic's ability to see the hypodermic needle and the volume scale on the syringe barrel.

It is also difficult for the visually impaired diabetic to align the hypodermic needle with the insulin bottle while avoiding being pricked, insert the hypodermic needle into the insulin bottle head to the proper depth, and to determine whether insulin or air is being drawn into the needle. This determination is critical because injecting air into one's body can be fatal.

Consequently, diabetics become increasingly reliant on caregivers as vision loss progresses to the point of total blindness. Such reduction of the person's independence can have severe psychological and emotional impact. With the availability of blood sugar machines that read blood sugar levels audibly and can be used by the visually impaired without assistance, and the invention described herein for drawing and injecting insulin, visually impaired diabetics will be able to lead more active, healthy, productive and normal lives.

The increase in infectious diseases throughout the world has caused a major concern for all health care workers with the possibility of these workers being accidentally wounded by the sharp needles used for hypodermic devices. This hazard exists both during the injection procedure and following the procedure while removing the needle from the injection site and disposing of the used hypodermic device. This has caused a huge problem in the disposal of used syringe needles. The problem of protection of the health care workers has caused such severe psychological and emotional disturbance among those concerned that many have now refused to deal with patients because of the possibility of contracting an infectious disease through their work.

Therefore, there is a need for a hypodermic device that is safe for use and disposal by health care workers, visually impaired diabetics, and other persons.

SUMMARY OF THE INVENTION

The present invention satisfies the above noted need by providing a hypodermic device having a retractable sleeve which, in an extended position, covers the hypodermic needle, and which retracts to allow the needle to enter the skin.

In a preferred embodiment of the invention, the sleeve is constructed as an adapter which engages the head of a medicine bottle and guides the needle into the bottle to the proper insertion depth to provide maximum use of the fluid to be drawn.

According to an aspect of the invention, the retractable sleeve is carried by the barrel of a syringe with the barrel passing slidably and axially through the sleeve. The needle end of the sleeve envelops the needle and protects accidental contact with the needle. The needle end of the sleeve is formed with an opening of a size and shape to accept the head of a medicine bottle and to guide the needle and bottle together in proper relationship to one another.

The needle end of the sleeve is further formed with an internal flange and tabs which cooperate to grasp the head of the medicine bottle and establish the correct insertion depth of the needle into the bottle.

The barrel of the syringe passes through the interior of a coil spring which extends between the sleeve and the finger flange at the plunger end of the barrel. The spring urges the sleeve toward the needle end of the barrel, yet allows the sleeve to be pushed back by the skin to enable the needle to penetrate into the skin. By this means a visually impaired person my turn the syringe with the bottle held in position so the fluid is at the bottom of the bottle and all the fluid can be drawn into the syringe, at most times eliminating the chance that air may be drawn into the syringe.

The syringe of the invention may also include a tactile feedback arrangement for allowing the user to sense the amount of medicine that has been drawn into the syringe barrel. For example, the syringe plunger may include serrations, and the barrel may includes a detent interfitting with the serrations. Each serration corresponds to a predetermined volume with the syringe barrel. Consequently, the user can determine the volume drawn into the needle by counting the "clicks" as the serrations move past and engage the barrel detent.

By drawing one tactile reading unit more than the desired amount, the user can then squeeze back one unit to feel if a drop has been emitted from the needle once the bottle has been disengaged from the needle and sleeve. With the syringe held upright, any air entrapped in the syringe will be at the needle end so that if fluid is not emitted the user will realize the syringe is not full and can use a new full bottle by injecting the fluid in the syringe into the new bottle and then repeating the filling procedure to assure the user that the syringe is full.

In an alternate preferred embodiment of the invention, the sleeve is open at the plunger end and the spring extends into the interior of the sleeve. The sleeve is formed with an internal rim against which the end of the spring abuts. From the internal rim, the sleeve extends toward the needle end. The sleeve slides over the syringe barrel with or without a positive attachment between the sleeve and the spring. With the spring in an uncompressed state, the needle end of the sleeve envelops the needle. The sleeve slides toward the plunger end, compressing the spring, to allow the needle to penetrate into skin.

In the alternate preferred embodiment, which is more suited for use by sighted health care givers or users, the sleeve or adapter is not needed to hold the bottle, but is instead designed to encapsulate or envelop the sharp needle when the needle is not needed to be exposed to either draw or inject fluid. The serrated plunger is also not needed, as the sighted health care giver or user can visually determine how much fluid is being drawn. As the needle is retracted from the bottle, the needle is again drawn back into the sleeve by the spring provided for this purpose. When the injection is to be given, the needle is again forced out of the end of the protective sleeve so it can enter the body of the patient. As the needle is withdrawn from the patient, the spring draws the needle back into the protective sleeve preventing the health care giver or user from being accidentally wounded. The end of the sleeve is preferably formed in a conical shape which tightens the skin at the point of injection; as a result, the health care giver or user does not need to place his or her hand or fingers near the point of injection.

With the needle completely encapsulated within the protective sleeve, protection of the waste handler is assured.

The invention may be provided as a fully assembled syringe, sleeve and spring. Alternatively, the sleeve and spring may be provided as a kit for assembly with an interchangeable, disposable syringe. Also, the invention is suitable for use with the hypodermic needle of an intravenous tube. The invention is fully usable by a visually impaired, and indeed blind, person.

These and other objects, advantages, and features of the invention will be more readily understood and appreciated by reference to the detailed description of the preferred embodiment and the drawings.

BRIEF DESCRIPTION OF THE DRAWINGS

FIG. 1 is a perspective view of a safety hypodermic syringe according to the principles of the invention;

FIG. 2 is a side view of the syringe, with the sleeve in axial section, in use with an insulin bottle;

FIG. 3 is a sectional view taken along the line III—III of FIG. 2;

FIG. 4 is a sectional view taken along the line IV—IV of FIG. 2;

FIG. 5 is a sectional view taken along the line V—V of FIG. 2;

FIG. 6 is a sectional view taken along the line VI—VI of FIG. 2;

FIG. 7 is a side view of the syringe, with the sleeve in axial section, with the needle inserted in skin;

FIG. 8 is a fragmentary side view, with the barrel in axial section, showing the tactile feedback structure;

DETAILED DESCRIPTION OF THE PREFERRED EMBODIMENT

Figure 12:
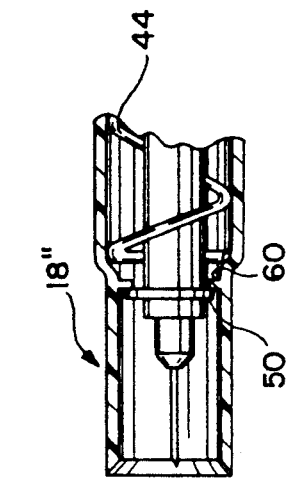
FIG. 12 is a fragmentary view of a safety hypodermic syringe according to a second alternate embodiment of the invention.

By way of disclosing a preferred embodiment of the invention, and not by way of limitation, there is shown in FIGS. 1 and 2 a safety syringe 10 which includes in its general organization a cylindrical barrel 12 having a plunger end 11 and a needle end 13, a plunger 14 which is slidable within the barrel, a hypodermic needle 16 affixed to the needle end of the barrel, an adapter sleeve 18, and a spring 20.

As is well known, the barrel 12 is formed as an elongated cylinder of transparent or translucent material and marked with volume indicia (not shown) along its length. The end of the barrel into which the plunger 14 is inserted is formed with a finger flange 21. The needle 16 is affixed to the opposite end of the barrel 12 in conventional fashion. The barrel 12 is formed with a flange 22 near the needle end.

The plunger 14 is formed as an elongated rod having a thumb rest 24 at its outer end and a resilient stopper (not shown) at its inner end which forms a fluid-tight seal with the inner wall of the barrel 12 in conventional fashion.

Referring to FIG. 8, the shaft of the plunger 14 may be formed with a series of spaced serrations or grooves 28 between ridges 29. These grooves are disposed at intervals corresponding to desired volumes or doses of medicine to be administered from the syringe. For example, the intervals between grooves may advantageously correspond to 2 units of U-100 insulin. The internal wall of the barrel is formed with resilient tabs 30 which extend into the plunger grooves 28, yet which yield to allow the plunger to be withdrawn and pushed in. The engagement and disengagement of the tabs with the grooves may be felt by the user, thus providing tactile feedback as to the amount of medicine drawn into, or dispensed from, the syringe.

Referring again to FIGS. 1–6, the sleeve 18 is carried on the barrel 12 at the needle end thereof. The sleeve is generally cylindrical, and coaxially surrounds the barrel. The end 34 of the sleeve disposed remotely from the finger flange 21 is open, and is dimensioned to receive the head H of a medicine bottle B (FIG. 2). Spaced axially inwardly from the end 34 of the sleeve, the inner wall of the sleeve is formed with three detents or tabs 36. Spaced an additional axial inward distance from the tabs 36, the inner wall of the sleeve is formed with an internal stop flange 38.

The stop flange 38 is spaced apart from the tabs 36 by a distance corresponding to the height of the medicine bottle head H. Together, the tabs 36 and stop flange 38 cooperate to form a zone for receiving and releasably grasping the medicine bottle head and for maintaining the bottle and needle in proper filling relationship. Preferably, the sleeve 18 is formed of plastic material such that the tabs 36 flex sufficiently to allow the bottle head H to be inserted until the end surface of the head contacts the stop flange 38. Further insertion of the bottle head is prevented by the stop flange. As shown in FIG. 2, tabs 36 engage the underside of bottle head H to maintain the bottle in engagement with the sleeve. The open end 34 is dimensioned to contact the shoulder S of the medicine bottle upon full insertion of the bottle into the sleeve as an additional means for aligning the bottle with the syringe.

The sleeve 18 is formed with a second internal stop flange 40 spaced apart from the stop flange 38 toward the finger flange 21. The stop flange 40 defines a central, circular opening having a diameter slightly larger than the outer diameter of the barrel 12. The stop flange 40 thus guides and centers the barrel within the sleeve 18 while allowing the sleeve and barrel to slide axially with respect to each other. The flange 22 of the barrel is disposed toward the needle 16 with respect to the stop flange 40. Flange 22 has an outer diameter greater than the inner diameter of stop flange 40 so as to prevent the barrel 12 from being withdrawn from the sleeve 18.

The end of the sleeve 18 nearest the finger flange 21 is formed with an end wall 42. End wall 42 is formed with a central circular opening of a diameter slightly larger than the outer diameter of the barrel 12 so as to guide the barrel for coaxial movement with respect to the sleeve.

The coil spring 20 extends from the sleeve 18 away from the needle end between the end wall 42 and the finger flange 21. The barrel is disposed coaxially in the interior of the spring. The coil spring 20 is dimensioned so as to be maintained in compression. The spring urges the sleeve toward the needle end of the syringe with the stop flange 40 in contact with the barrel flange 22. When the syringe is not in use, the spring will thus maintain the sleeve in the extended position shown in FIG. 1 in which the sleeve envelops the needle and protects against needle pricks.

When the syringe is to be filled, the user may grasp the sleeve and guide the medicine bottle head into the sleeve by his or her fingers. The sleeve will automatically align the bottle head with the needle while at the same time protecting the user's fingers from the needle.

As shown in FIG. 2, the sleeve is arranged so that the needle tip enters only a short distance into the medicine bottle B. In this manner, with the bottle inverted, the likelihood of drawing air into the syringe is minimized.

FIG. 7 illustrates the use of the safety syringe 10 to inject medicine through skin D. The open end 34 of the sleeve 18 is placed against the skin at the injection site. The barrel 12 is then pushed toward the skin. The spring 20 is compressed, allowing the barrel to slide through the sleeve and the needle to pierce the skin while the sleeve is in a retracted position and the needle extends beyond the sleeve. When the injection is completed, the barrel and needle are withdrawn, and spring 20 causes the sleeve to return to its protective position enveloping the needle.

Figure 11:
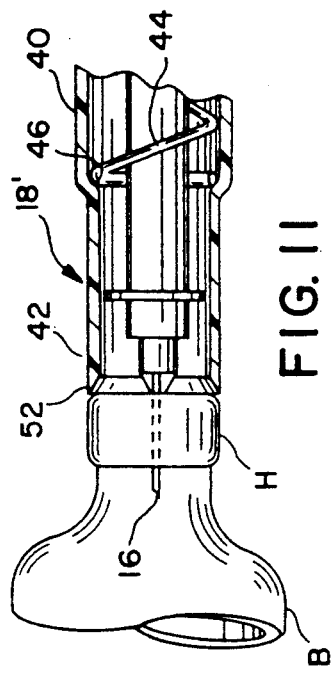
FIG. 11 is a fragmentary view of the syringe of FIG. 9, with the sleeve in axial section, and the needle inserted in a medicine bottle.
Figure 10:
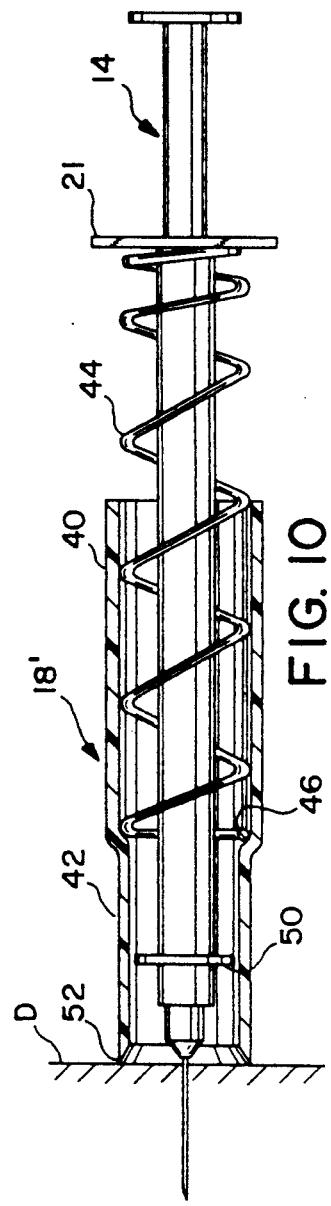
FIG. 10 is a side view of the syringe of FIG. 9, with the sleeve in axial section, and the needle inserted in skin.
Figure 9:
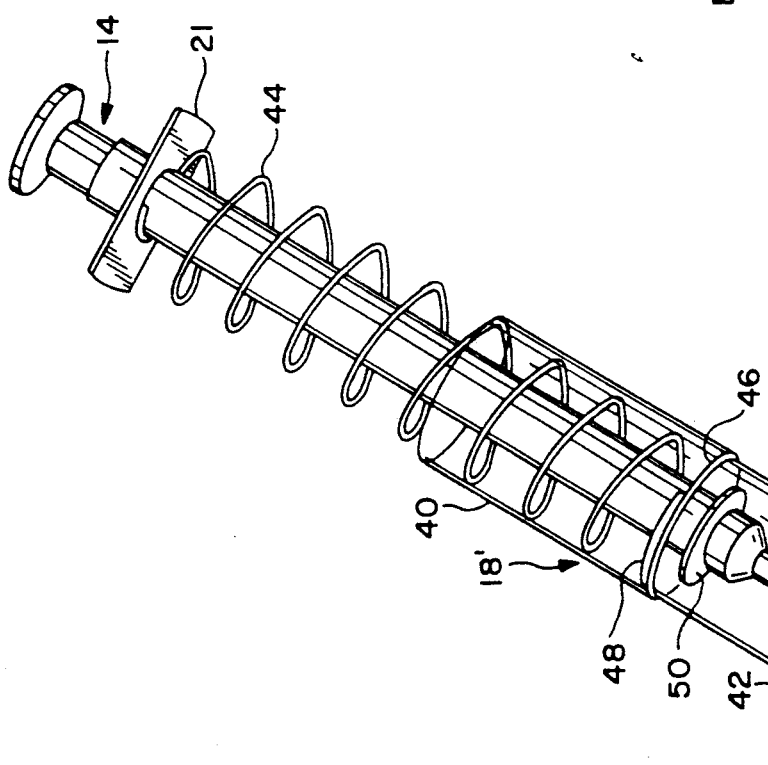
FIG. 9 is a perspective view of a safety hypodermic syringe according to an alternate embodiment of the invention.

FIGS. 9–11 illustrate an alternate embodiment of the invention. In this embodiment, the sleeve 18 is formed as a cylinder having a plunger end portion 40 and a needle end portion 42. The plunger end portion 40 is of an inner diameter large enough to allow the spring 44 to extend within the plunger end portion of the sleeve. Thus, the portion of the spring nearest the needle end of the syringe is encapsulated or enveloped by the plunger end portion 40 of the sleeve.

The needle end portion 42 of the sleeve is formed with an inner diameter somewhat less than the inner diameter of the sleeve end portion 40, thus forming an internal rim 46 at the juncture of the plunger end portion and the needle end portion. In this embodiment, as shown in FIG. 11, the open needle end 52 of the sleeve is preferably dimensioned with a diameter approximately equal to the diameter of the head H of a medicine bottle B. Thus, when the needle 16 is inserted into a medicine bottle, the sleeve abuts against the bottle head H and is pushed up the barrel of the syringe by the bottle head. Spring 44 is compressed between the sleeve rim 46 and the finger flange 21.

The needle end of the syringe barrel is formed with a flange 50 of a diameter slightly less than the inner diameter of the needle end portion 42 of the sleeve. Flange 50 and spring 44 cooperate with the inner wall of the sleeve to guide and maintain the sleeve in coaxial alignment with the sleeve 18.

The needle end 52 of the sleeve 18 is advantageously formed with an internal frusto-conical taper. When the sleeve is urged against the skin D by spring 44 as shown in FIG. 10, the conical shape of the sleeve end and the force exerted by the spring 44 act to draw the skin tight and facilitate penetration by the needle.

The spring 44, sleeve 18, and the syringe may be provided without interattachments so that the sleeve and spring may freely slide on and off the needle end of the syringe. Alternatively, a suitable attachment may be provided between the spring and sleeve at the rim 46 and between the spring and the syringe at the finger flange 21 to maintain the spring and sleeve in assembly with the syringe.

As shown in FIG. 9, the sleeve 40 may be extended toward the needle end of the syringe in a position similar to that shown in FIG. 2 in which the needle end portion 42 envelops and protects the needle 16. The spring 44 is dimensioned such that when the sleeve is in the extended position, the spring will be in an uncompressed, relaxed state, thus preventing the spring from urging the sleeve off the syringe barrel.

Additionally, as shown in FIG. 12, sleeve 18 may be formed with an internal flange 60 having an inner diameter less than the outer diameter of flange 50. Flange 60 contacts flange 50 to prevent the syringe from being withdrawn from the sleeve. With this arrangement, spring 44 is preferably always in compression to urge the sleeve 18 into a protective position enveloping the needle.

The invention is suited for use with an intravenous line. The barrel will comprise an intravenous needle holder and the plunger will be absent. A flexible intravenous tube will be connected to the needle holder. The sleeve will be placed over the intravenous needle holder and envelop the needle except when the needle is inserted into a patient. A suitable flange may be provided on the tube or needle holder with a spring extending between the sleeve and flange as described above.

The invention may be provided as an assembly of the syringe, spring, and sleeve. Alternatively, the invention may be provided as a kit including a sleeve and spring to be assembled to separately purchased, disposable syringes, or as a kit including an unassembled sleeve, spring, and syringe. All of the embodiments described herein are suitable for use as disposable products.

It will be readily understood and appreciated that the various embodiments of the invention provide a means for a visually impaired person, such as a diabetic, to give himself a hypodermic injection. The tactile response provided by the present invention eliminates the need for the user to visually observe the location of the plunger stopper within the barrel. The present invention therefore greatly increases the independence of a visually impaired diabetic. The invention further provides health care givers a high degree of protection against accidental wounding before, during, and after the use of a hypodermic device.

The above descriptions are those of preferred embodiments of the invention. Various alterations and changes can be made without departing from the spirit and broader aspects of the invention as set forth in the appended claims, which are to be interpreted in accordance with the principles of patent law including the doctrine of equivalents.

The embodiments of the invention in which an exclusive property or privilege is claimed are defined as follows:

1. A hypodermic syringe comprising:
   a barrel having a plunger end and an axially opposite needle end;
   a hypodermic needle affixed to said needle end;
   a plunger slidable within said barrel for filling said barrel with medicine and for dispensing medicine from the barrel;
   a sleeve carried on the needle end of said barrel for axial movement therealong, said sleeve having a first end portion disposed proximate said needle end, and a second end portion disposed proximate said plunger, said barrel passing through said second end portion, said sleeve disposed coaxially with said barrel and being movable between an extended position in which said needle is enveloped by said sleeve and a retracted position in which said needle extends beyond said sleeve, said first end portion having a size and shape to accept the head of a medicine bottle when said sleeve is in said extended position, said sleeve including means for maintaining said medicine bottle in filling engagement with said head, said sleeve further including a flange means formed in the interior of said sleeve and resilient tab means formed in the interior of said sleeve axially spaced apart from said flange means, said tab means disposed between said open end and said flange means, whereby when said sleeve is in said extended position said needle is protected against contact therewith, and whereby when said sleeve is in said retracted position said needle may enter a person's skin for injection of medicine, and whereby the head of said medicine bottle may be releasably grasped between said tab means and said flange means.

2. The hypodermic syringe of claim 1 wherein said flange means, said tab means, and said hypodermic needle are arranged such that when the head of said medicine bottle is grasped between said tab means and said flange means, said hypodermic needle is disposed within said medicine bottle at a depth that helps to avoid introduction of air from said bottle into said syringe.

3. The hypodermic syringe of claim 1 wherein said barrel is formed with an external flange disposed near said needle end and said sleeve is formed with an internal flange, said external flange having an outer diameter greater than said internal flange inner diameter, whereby said external flange and said internal flange interengage to prevent said barrel from being withdrawn from said sleeve.

4. The hypodermic syringe of claim 1 further comprising a spring carried on said barrel and extending between said sleeve and said plunger end, said spring urging said sleeve toward said extended position.

5. The hypodermic syringe of claim 1 further comprising means for providing tactile feedback as to the relative movement between said plunger and said barrel.

6. The hypodermic syringe of claim 1 wherein said first end portion has a diameter substantially equal to the diameter of the head of a medicine bottle.

7. A safety syringe kit comprising:
   a sleeve adapted to be carried on the barrel of a hypodermic syringe for axial movement therealong, said sleeve having a diameter greater than the diameter of said barrel, said sleeve having a first, open end to be disposed proximate the needle end of the syringe, and a second end to be disposed proximate the plunger end of the syringe with the barrel of said syringe passing through said second end, said sleeve to be disposed coaxially with said barrel and being movable between an extended position in which the needle of the syringe is enveloped by said sleeve and a retracted position in which the needle extends beyond said sleeve, whereby when said sleeve is in said extended position the needle is protected against unwanted contact therewith, and whereby when said sleeve is in said retracted position said needle may enter a person's skin for injection of medicine, said sleeve formed with a plurality of internal resilient tabs disposed axially inwardly from said open end of said sleeve, and a first internal flange disposed further axially inwardly from said internal tabs, said tabs and said first internal flange cooperating to releasably grasp the head of a medicine bottle inserted into said open end and maintain the bottle in proper filling relationship with the needle of the syringe; and
   a spring adapted to be carried on the barrel of said syringe between said sleeve and the plunger end of the syringe for urging said sleeve toward said extended position.

8. The safety syringe kit of claim 7 wherein said sleeve includes an internal rim forming an abutment against which said spring urges said sleeve toward said extended position.

* * * * *